United States Patent [19]

Ingersoll et al.

[11] Patent Number: 4,943,483
[45] Date of Patent: Jul. 24, 1990

[54] PALLADIUM ALLOY CONTAINING GOLD, SILVER, GALLIUM, GERMANIUM AND/OR LITHIUM AND DENTAL RESTORATIONS UTILIZING SAME

[75] Inventors: Clyde E. Ingersoll, Tonawanda; Stephen P. Schaffer, Hamburg; Patrick J. McCabe, Tonawanda, all of N.Y.

[73] Assignee: Williams Dental Company, Inc., Buffalo, N.Y.

[21] Appl. No.: 301,139

[22] Filed: Jan. 25, 1989

[51] Int. Cl.$^5$ .......................... B32B 15/04; C22C 5/04
[52] U.S. Cl. ..................................... 428/433; 420/463; 433/200.1; 433/207; 428/469
[58] Field of Search ................. 420/463; 428/433, 469; 433/200.1, 207

[56] References Cited

U.S. PATENT DOCUMENTS

| | | | |
|---|---|---|---|
| 4,201,577 | 5/1980 | Ingersoll et al. | 420/508 |
| 4,350,526 | 9/1982 | Schaffer | 420/463 |
| 4,399,096 | 8/1983 | Agarwal et al. | 420/463 |
| 4,569,825 | 2/1986 | Dvivedi et al. | 420/464 |
| 4,836,984 | 6/1989 | Wagner et al. | 420/464 |

FOREIGN PATENT DOCUMENTS 61-186437  8/1986  Japan ................................. 420/464

OTHER PUBLICATIONS

Tucillo, "Palladium Alloys ... Todays Choice for PFM Restorations", *Trends and Techniques*, Nov. 1987, pp. 14 & 31.

*Primary Examiner*—John F. Niebling
*Assistant Examiner*—Margery S. Phipps
*Attorney, Agent, or Firm*—Waldron & Associates

[57] ABSTRACT

Dental restorations are made of a high palladium alloy which consists essentially of, on a weight basis, 70–82 percent palladium; 5–8 percent gold; 6.5–8 weight percent silver; 5–9 percent gallium; from 4 to 8 weight percent of a surface oxide producing modifier selected from the group consisting of indium, tin and mixtures thereof, from 0.01 up to 2 percent, ordinarily less than about 0.5 percent, of an oxygen scavenging component which is a member selected from the group consisting of germanium, lithium and mixtures thereof; and up to 2 percent of a grain refiner selected from the group consisting of ruthenium, rhenium and iridium. Alloy can be melted without the need of shielding the alloy from the atmosphere.

10 Claims, No Drawings

PALLADIUM ALLOY CONTAINING GOLD, SILVER, GALLIUM, GERMANIUM AND/OR LITHIUM AND DENTAL RESTORATIONS UTILIZING SAME

BACKGROUND OF THE INVENTION

1. Field of the Invention

This invention relates to the field of noble metal alloys and to their use in the manufacture of dental restorations, and more specifically relates to a new and improved high palladium alloy containing gold, and silver, which does not discolor porcelain, has an excellent combination of physical properties for use in combination with porcelain and can be readily worked at melting temperatures without the need for special shielding atmospheres.

2. The Prior Art

As is well known, dental casting alloys should provide a high degree of biocompatibility or inertness to the conditions in the mouth and good physical properties so that they will provide long lived usage. In addition, those alloys which are used to provide castings upon which porcelain coatings may be applied must provide good bonding characteristics to the porcelain coatings, with little or no loss of strength at porcelain firing temperatures and other characteristics which are compatible with the porcelain coatings, such as similar coefficient of thermal expansion, avoidance of discoloration of the porcelain, etc. Lastly, the alloy should process well during casting and be useful with commercially available porcelains.

Previously, gold alloys, usually gold/platinum alloys, were preferred as dental casting materials for porcelain applications because they have provided a highly desirable balance of properties. The commercially available dental porcelains have been formulated so as to be compatible therewith.

Over the years, much effort has gone into developing alloys for dental applications with higher strength and lower cost (more readily available) metals. For example, cobalt base alloys almost completely displaced gold alloys in the area of partial dentures in the mid 1930s. And, more recently, nickel base alloys have made a significant impression in porcelain substrate alloys.

Within the noble metals area, much effort has been expended to use the nobility, strength and lower cost of palladium as the base for new alloy systems. In the 1930s, high palladium and palladium based alloys were attempted, but the need to deoxidize palladium was not recognized. The problems with high palladium alloys was believed, until recently, to be hydrogen dissolved therein.

A number of gold/palladium and palladium/silver alloys have been developed which provide a high degree of compatibility with porcelain and satisfactory physical and mechanical properties. However, silver has a tendency to migrate at the porcelain firing temperature and to discolor the porcelain. This silver migration and its discoloration of porcelain make porcelain selection and porcelain firing control critical in order to produce aesthetic porcelain fused to alloy restorations, particularly for anterior use.

While reduction or elimination of silver content minimized the discoloration effect, it made control of the alloy thermal expansion (contraction) more difficult. Elimination of gold has had the same effect on thermal expansion characteristics. Nevertheless, silver and gold are elements which are very useful in formulating alloys with the desirable coefficient of thermal expansion for compatibility with porcelain, about $13.8-15 \times 10^{-6}$ in/in/° C. In one of co-applicant's prior applications, Ser. No. 174,749 filed Aug. 4, 1980, now U.S. Pat. No. 4,350,526, there is disclosed a palladium alloy which has overcome the discoloration problem.

However, even the palladium alloys of co-applicant's patent require close control in the porcelain firing step and selection of the porcelains used in connection therewith. The generally available dental porcelains were formulated for use with high gold content alloys so as to exhibit a coefficient of thermal expansion which is typically 5-10 percent lower than the high gold content alloys This results in placing the porcelain coating in compression after cooling from the firing temperature, thereby producing a stronger restoration when it is subjected to tensile loading.

The reduction or elimination of the gold content in some of the substitute alloys has caused difficulty in maintaining a sufficiently high thermal coefficient of expansion, which is desirably in the range of $13.8-15 \times 10^{-6}$in/in/° C. As indicated in co-applicant's above identified patent, silver has been used to replace gold in an effort to provide a suitable coefficient of thermal expansion but it tends to migrate at the porcelain firing temperatures, and to cause a distinct uncontrolled discoloration of the porcelain which is aesthetically unacceptable.

Another more recently developed high palladium alloy is one essentially containing both gold and silver at about 6 weight percent gold, 6.5 weight percent silver and no copper or cobalt. Because of the relatively low silver content, the alloy produces a light grey oxide which does not discolor porcelain on firing. Although the gold content is also rather low, it does enhance the alloy's properties to some extent, but the alloy is still characterized by an inadequate coefficient of thermal expansion, often causing cracking on porcelains fired thereon. As with most prior art palladium alloys, moreover, this gold and silver containing alloy is subject to considerable oxygen absorption in the molten state so that precautions must be taken to shield the molten alloy from the atmosphere during high temperature processing and fabrication.

Alloys for use as ceramo-metal restorations must also exhibit a desired balance of physical and mechanical properties. To properly support the fragile porcelain layer or the restoration, the alloy must have a yield strength, at 0.1 percent offset, of over 40,000 psi. In addition, the alloy needs high temperature strength to withstand the forces applied to the restoration while the porcelain is being fired in place.

While standard tensile tests are possible at porcelain firing temperatures, 950°-1000° C., a more reliable test of strength for the special circumstances of porcelain fired to metal dental restorations is the "sag" test. This test is performed on a strip of alloy $1 \times 10$ mm in cross section and 50 +mm long. The strip is supported on knife edge supports 50 mm apart and a static load applied. The assembly is placed in a standard dental porcelain firing furnace and heated in the same manner as a normal dental restoration. The amount of deflection is measured and this "sag" is an indication of the high temperature strength of the alloy. Sag in the 5 mm range is unacceptable. Sag of from 1-5 mm requires special precautions be made to prevent detrimental sag when a three or more unit bridge is being fired. The desired value is less than 1 mm.

Moreover, a dental casting alloy must be able to be soldered before the porcelain firing cycle. Since porcelain is fired at approximately 1000° C., the alloy must possess a solidus above about 1100° C. to allow the solder to flow without starting to melt the casting. However, in order to allow the alloy to be cast with standard equipment found in dental laboratories, the liquidus temperature must not be greater than about 1400° C. Lastly, the alloy must also exhibit good bonding to dental porcelains.

Many palladium based and high palladium content alloys may meet the physical and mechanical requirements noted but are completely unusable due to a certain characteristic of palladium. Palladium has a high affinity for oxygen, and much of the early failure to develop high palladium alloys was the failure to recognize this problem.

SUMMARY OF THE INVENTION

This invention is predicated upon the development of a new and improved high palladium alloy containing gold and silver comparable to that of the prior art but which further contains an oxygen scavenger selected from the group consisting of germanium, lithium and mixtures thereof, with or without other specific alloy additives. The improved alloy of this invention does not discolor porcelain, has an excellent combination of physical properties for use in combination with porcelain, including a coefficient of thermal expansion adequate to virtually eliminate cracking of porcelains fired thereon, can be readily worked at melting temperatures without the need for special shielding atmospheres and exhibits an exceptional high degree of bond strength when bonded to porcelain.

In addition to the above very useful properties, the alloys of this invention form a desirable surface oxide coating which serves to enhance the bonding of the alloys to porcelain, and additionally exhibit a highly desirable balance of casting properties and physical properties, together with biocompatibility. The alloys of this invention may be cast and soldered relatively easily and form excellent dental restorations with porcelain coatings fired thereon.

It has now been found that the foregoing and related advantages may be readily attained in a high palladium alloy which consists essentially of, on a weight basis, about 75 percent palladium, about 6 percent gold, at least about 6.5 percent silver, about 6 to 7 percent gallium, ordinarily from about 0.01 to 2 percent of an oxygen scavenging component which is a member selected from the group consisting of germanium, lithium and mixtures thereof and about 5 percent of a surface oxide producing modifier selected from the group consisting of indium, tin and mixtures thereof. Additionally, the alloy may contain from 0.05 up to 2 percent of a grain refining component which is a member selected from the group consisting of ruthenium, rhenium, iridium and mixtures thereof. The alloy is free of nickel, cobalt, copper and boron.

Considering the composition more broadly, the palladium, gold, silver, gallium and indium contents are essentially the same as those utilized in the prior art alloy, wherein the palladium content is desirably in the range of 70-82 percent by weight of the alloy, and ideally about 75 percent. The gold content is preferable within the range 5 to 8 weight percent and ideally about 6 percent. The silver content is preferable within the range 6.5 to 8 weight percent and essentially no less than 6.5 percent. Gallium is included within the range of about 5 to 9 weight percent, and ideally about 6 to 7 percent. To provide an oxide on the surface of the alloy to which porcelain may bond, an oxidizer, e.g. indium and/or tin is included within the range of about 4 to 8 weight percent, and preferably about 6 weight percent. The oxygen scavenger, e.g. germanium and/or lithium is provided in an amount not normally exceeding 2 weight percent. Rhenium, ruthenium and/or iridium can be provided as a grain refiner in amounts up to 2 weight percent, but preferably up to 0.5 weight percent.

A highly advantageous alloy is one containing about 75 weight percent palladium, about 6 weight percent gold, 6.5 weight percent silver, about 6 weight percent gallium, 6 weight percent indium, with the oxygen scavenging component being about 0.01 weight percent lithium, and further containing about 0.3 percent ruthenium.

The dental restorations comprise a casting of the aforementioned alloy and a porcelain coating fired upon a portion of the casting. The porcelain coatings are substantially free from discoloration and are firmly bonded to the casting.

DETAILED DESCRIPTION OF THE PREFERRED EMBODIMENTS

As hereinbefore indicated, the alloys of the present invention use palladium as the principal component, and use gold, silver, indium and gallium as the other essential components. The alloys also essentially contain a small amount of the oxygen scavenging component and may contain grain refining components, namely rhenium, ruthenium and/or iridium.

The alloys of this invention must contain at least 70 weight percent palladium and may contain as much as 82 weight percent palladium. Preferably, the alloy contains 74-76 weight percent palladium in order to obtain the optimum balance of properties, while maintaining the desired nobility.

The gold content may vary from 5-8 percent by weight of the total composition and is preferably in the range of 5.5-6.5 percent by weight with the ideal content being about 6 percent. The gold contributes to the alloy's nobility and in combination with the silver content, provides the desired coefficient of thermal expansion and contraction.

The silver content may vary from 6.5-8 percent by weight of the total composition and is preferably in the range of 6.5-7 percent by weight with an essential content of at least 6.5 percent. The silver contributes to the alloy's nobility and physical properties, if present in amounts of at least 6.5 percent, but amounts in excess of 8 percent may tend to discolor any porcelain fired adjacent thereto.

Gallium in amounts of 5 to 9 weight percent provides strength to the resulting alloy and contributes to the control of thermal expansion and to surface oxide formation as desired for porcelain bonding. The preferable concentration is about 6 weight percent. Concentrations above 6 to 9 weight percent will increase the alloy's brittleness and lower the solidus temperature. Concentrations below 4 to 6 weight percent causes a lowering of mechanical properties and lowers the coefficient of thermal expansion.

Indium and/or tin in a concentration of 4 to 8 weight percent provides strength to the alloy and a surface oxide formation to promote porcelain bonding. The preferable concentration of indium and/or tin is about 6 weight percent, as concentrations above 6 to 8 weight percent increases brittleness, while concentrations below 4 to 6 weight percent will lower mechanical properties and reduce the surface oxidation to adversely effect porcelain bonding.

From 0.01 up to 2 percent, but generally less than about 0.2 percent, of an oxygen scavenging element, which is a member selected from the group consisting of germanium, lithium, and mixtures thereof is desirably added and preferably in the range of 0.1–0.2 percent to serve as a scavenger for oxygen and oxides either present in the alloy or formed during the casting process.

When the amount of the oxygen scavenging component, whether germanium, lithium, or a mixture of both, is employed in excess of about 2 percent of the alloy, an embrittling effect is encountered. It is generally not preferred to add the component in amounts greater than required to afford the necessary degree of oxygen scavenging.

For most applications, it is desirable to incorporate ruthenium, rhenium and/or iridium in an amount of up to 0.5 percent by weight in order to effect grain refinement. When such a grain refining component is included, it is preferably present in the range of 0.1–0.5 percent.

The alloys produced in accordance with the present invention routinely exhibit a solidus temperature in excess of 1100° C. in order to withstand porcelain firing temperatures of about 1000° C., while the liquidus temperature of the alloy is well below 1400° C. to permit facile processing in the equipment generally available in dental laboratories. To provide a good compatible alloy for use with present commercial porcelains, the alloy has a coefficient of thermal expansion within the range of $13.8–15 \times 10^{-6}$ in/in/° C. (600°–20° C.). The yield strength of the alloy at 0.1 percent offset is in excess of 40,000 psi. The sag is normally below 1 mm. Moreover, the alloys of the present invention have both high corrosion resistance and tarnish resistance and do not discolor the porcelain.

Illustrative of the efficacy of the alloys of the present invention are the following examples, wherein all percentages are by weight unless otherwise indicated.

EXAMPLE ONE

An alloy was prepared containing the following in weight percent: 75.19 percent palladium, 6 percent gold, 6.5 percent silver, 6.0 percent gallium, 6.0 percent indium, 0.3 percent ruthenium and 0.01 percent lithium. Specimens cast therefrom were found to exhibit the following properties: Sag, 0.800 mm; melting range, 2320° to 2390° F.; yield strength at 0.1% offset, 68,700 psi; modulus of elasticity $15.0 \times 10^6$; elongation 34.0 percent and coefficient of thermal expansion, $14.30 \times 10^{-6}$ in/in/° C.

EXAMPLE TWO

An alloy was prepared COntaining the following in weight percent 75.2 percent palladium, 6 percent gold, 6.5 percent silver, 6.0 percent gallium, 6.0 percent indium and 0.3 percent ruthenium. Specimens cast therefrom were found to exhibit a sag value of 2.40 mm. This value can be attributed to porosity, due to the absence of an effective oxygen scavenger.

I claim:
1. A dental alloy consisting essentially of:
   a. 70–82 percent by weight palladium;
   b. 5–8 percent by weight gold;
   c. 6.5–8 percent by weight silver;
   d. 5–9 percent by weight gallium;
   e. 4–8 percent by weight of a surface oxide producing modifier selected from the group consisting of indium, tin and mixtures thereof;
   f. from about 0.01 up to about 2 percent by weight of an oxygen scavenging component which is a member selected from the group consisting of germanium, lithium, and mixtures thereof; and
   g. up to 2 percent by weight of a grain refiner selected from the group consisting of ruthenium, rhenium, iridium, and mixtures thereof, said alloy capable of being heated and melted without the need for shielding the alloy from the atmosphere, and having a coefficient of thermal expansion of about $14.0–15 \times 10^{-6}$ in/in/° C., a solidus temperature of at least 1100° C., a liquidus temperature of not more than 1400° C., Vickers hardness greater than 150, offset yield strength at 0.1 percent offset of greater than 40,000 p.s.i., tensile elongation greater than 6 percent and a sag of less than 1 mm.

2. The dental alloy of claim 1 containing from 0.05 to 0.5 weight percent of the grain refiner selected from the group consisting of ruthenium, rhenium, iridium and combinations thereof.

3. The dental alloy of claim 1 containing from 0.1 to 0.5 weight percent of the grain refiner selected from the group consisting of ruthenium, rhenium, iridium and combinations thereof.

4. The dental alloy of claim 1 wherein the oxygen scavenging component content is 0.01–0.2 percent.

5. The dental alloy of claim 1 wherein the surface oxide producing modifier content is about 5 weight percent.

6. The dental alloy of claim 1 wherein the palladium content is 74–76 percent, the gold content is 5.5–6.5, the silver content is 6.5–7, and the gallium content is 6–7 percent.

7. A dental restoration comprising:
   a. a casting of a dental alloy consisting essentially of
      (i) 70–82 percent by weight palladium;
      (ii) 5–8 percent by weight gold;
      (iii) 6.5–8 percent by weight silver;
      (iv) 5–9 percent by weight gallium;
      (v) 4–8 percent by weight of a surface oxide producing modifier selected from the group consisting of indium, tin and mixtures thereof;
      (vi) from about 0.01 up to about 2 percent by weight of an oxygen scavenging component which is a member selected from the group consisting of germanium, lithium, and mixtures thereof; and
      (vii) up to 2 percent by weight of a grain refiner selected from the group consisting of ruthenium, rhenium, iridium, and mixtures thereof;
   said alloy having a coefficient of thermal expansion of about $14.0–15 \times 10^{-6}$ in/in/° C., a solidus temperature of at least 1100° C., a liquidus temperature of not more than 1400° C., Vickers hardness greater than 150, offset yield strength at 0.1 percent offset of greater than 40,000 p.s.i., and tensile elongation greater than 6 percent; and
   b. a porcelain coating upon a portion of said casting, said coating being firmly bonded to said casting and being substantially free from discoloration.

8. The dental alloy of claim 7 containing from 0.01 to 0.1 weight percent of a grain modifier selected from the group consisting of ruthenium, rhenium, iridium and combinations thereof.

9. The dental restoration of claim 7 wherein the oxygen scavenging component content is 0.1–0.2 percent.

10. The dental restoration of claim 7 wherein said alloy contains 74–76 percent by weight palladium, 5.5–6.5 percent by weight gold, 6.5–7 percent by weight silver, 6–7 percent by weight gallium, and 5–6 weight percent surface oxide producing modifier.

* * * * *